United States Patent [19]
Alford

[11] 3,937,825
[45] Feb. 10, 1976

[54] ANTHELMINTIC COMPOSITION AND METHOD OF USE

[75] Inventor: Booker Taliaferro Alford, Trenton, N.J.

[73] Assignee: American Cyanamid Company, Stamford, Conn.

[22] Filed: Oct. 15, 1974

[21] Appl. No.: 514,726

Related U.S. Application Data

[63] Continuation-in-part of Ser. No. 399,651, Sept. 21, 1973, abandoned.

[52] U.S. Cl................................ 424/217; 424/270
[51] Int. Cl.$^2$.......................................... A61K 31/66
[58] Field of Search............................ 424/217, 270

[56] References Cited
UNITED STATES PATENTS

| | | | |
|---|---|---|---|
| 3,111,457 | 11/1963 | Trace et al.......................... | 424/217 |
| 3,679,725 | 7/1972 | Bullock.............................. | 424/270 |

*Primary Examiner*—V. D. Turner
*Attorney, Agent, or Firm*—Denis A. Polyn

[57] ABSTRACT

An anthelmintic composition comprising a combination of 0,0-dimethyl (2,2,2-trichloro-1-hydroxyethyl)-phosphonate and 1-6-phenyl-2,3,5,6-tetrahydroimidazo[2,1-b]thiazole hydrochloride and a method for control of gastrointestinal, cutaneous and lung-infesting parasites in equine species.

2 Claims, No Drawings

ANTHELMINTIC COMPOSITION AND METHOD OF USE

This application is a continuation-in-part of my application Ser. No. 399,651, filed Sept. 21, 1973, now abandoned.

FIELD OF THE INVENTION

This invention relates to anthelmintic compositions and a method for controlling internal parasites in equine species.

DESCRIPTION OF THE PRIOR ART

The control of internal animal parasites by the use of drugs or drug combinations can be a difficult problem because drugs must be toxic to the parasites and non-toxic to the host. Thus, the discovery of a drug or drug combination effective for the control of gastrointestinal, cutaneous and lung-infesting parasites is difficult because of these adverse requirements.

The organophosphorus compound, 0,0-dimethyl (2,2,2-trichloro-1-hydroxyethyl)phosphonate, (a component of the present invention) hereinafter referred to as "trichlorfon," is useful for the removal of bots (*Gasterophilus intestinalis* and *Gasterophilus nasalis*), ascarids (*Parascaris equorum*) and pinworms (*Oxyuris equi*) from mammals such as horses when administered at the recommended dosage of 40 mg./kg. body weight. At this dosage level, however, 0,0-dimethyl (2,2,2-trichloro-1-hydroxyethyl)phosphonate has only about 30% efficacy against small strongyles and only about 5–10% efficacy against large strongyles [*Equine Medicine and Surgery: A Text and Reference Work*, page 169 (1970), published by American Veterinary Publications, Inc., 114 North West Street, Wheaton, Illinois]. Since trichlorfon is quite toxic to mammals, higher dosages are not recommended if toxic manifestations are to be avoided.

The other component of the present compositions, 1-6-phenyl-2,3,5,6-tetrahydroimidazo [2,1-b]thiazole hydrochloride, also referred to herein after as "levamisole hydrochloride," is an anthelmintic which is very effective for the removal of ascarids, pinworms and the most pathogenic large strongyle, *Strongylus vulgaris*. By itself, levamisole hydrochloride is somewhat less effective in the removal of the large strongyle, *Strongylus edentatus*. The efficacy of 1-6-phenyl-2,3,5,6-tetrahydroimidazo [2,1-b]thiazole hydrochloride against small strongyles when administered to horses (Clarkson et. al., *Annals of Tropical Medicine and Parasitology*, Volumn 65, No. 1, 1971) is not uniformly high even at a dose of 20 mg./kg. The mean efficiency of levamisole hydrochloride was 13.0% at 7.5 mg./kg. (two animals); 5.6% at 10.0 mg./kg. (two animals); 61.4% at 15 mg./kg. (four animals); and 63.4% at 20 mg./kg. (seven animals). At the dosage levels of 20 mg./kg., or higher, the resulting toxicosis produces profuse sweating, lacrimation and hyperexcitability.

DESCRIPTION OF THE INVENTION

It has been found that by combining trichlorfon with levamisole hydrochloride, there is obtained a combination that is particularly useful in that it has excellent efficacy against small strongyle without evidencing increased mammalian toxicity.

The present invention provides an anthelmintic for equine species, particularly horses, donkeys, ponies, burrows, and mules, comprising trichlorfon and levamisole hydrochloride in a weight ratio of from about 2 to 5 parts by weight of trichlorfon to each part by weight of levamisole hydrochloride. The composition of this invention is especially useful in the control of ascarids, bots, large strongyles and pinworms, in various animals infested therewith, particularly in the control of small strongyles in horses. The present compositions are also effective for controlling cutaneous parasites such as *Habronema muscae*, *H. microstoma*, *H. draschia* and lung parasites such as *Dictyocaulus arnfieldi*.

It was further found that excellent results are obtained in equine species such as horses by the oral administration of a combination of about 40 mg./kg. body weight of trichlorfon and 8 mg./kg. body weight of levamisole hydrochloride.

The composition of this invention may be administered orally, or may be injected intravenously, subcutaneously, or intraperitoneally. Oral administration may be in the form of (1) a powder that can be mixed in the feed, (2) a bolus administered by means of a balling gun, (3) a mixture either dissolved or dispersed in water and administered by means of a stomach tube or drench, (4) a dose syringe such as used to administer a paste, and (5) a mash or pelleted feed formulation.

The desired therapeutic effect of the combination of trichlorfon and levamisole hydrochloride may also be obtained by administering the anthelmintics separately but in an immediate sequential manner rather than as a mixture to obtain similar results.

In practice, the anthelmintic composition of this invention will generally be formulation with conventional solid or liquid adjuvants or formulation aids. Illustrative of the preparation of such an anthelmintic composition is the following:

Components A and B are prepared separately by blending the following solid ingredients together:

| Composition of Component A | |
| --- | --- |
| Ingredient | Percent by Weight |
| Trichlorfon | 47.6 |
| Cab-o-Sil (fused silica) | 0.1 |
| Dextrose, anhydrous | 52.3 |

| Composition of Component B | |
| --- | --- |
| Ingredient | Percent by Weight |
| Levamisole . HCl | 15.4 |
| Cab-o-Sil | 0.1 |
| Lactose, anhydrous | 84.5 |

At a dosage level of 8 mg. of levamisole hydrochloride per kilogram of animal body weight and 40 mg. of trichlorfon per kilogram of animal body weight, one would use 9.56 grams of Composition of component A with 5.92 grams of Composition of component B for each 250 pounds of animal body weight to be treated. The total daily dose of anthelmintics based on ratio of 5 to 1 trichlorfon to levamisole may vary from 4 grams to about 40 grams depending on the weight of the animal.

The active components of this invention can be used in other equine species as ingredients of compositions such as tablets; the principal active components are mixed with conventional tableting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two component compositions can be separated by an enteric layer which serves to resist disintegration in the stomach and permits the inner portion to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for equine species, each unit containing a predetermined quantity of active components calculated to produce the desired therapeutic effect in association with the required pharmaceutical diluent, carrier or vehicle. The specification for the novel dosage forms of this invention are indicated by characteristics of the active components and the particular therapeutic effect to be achieved or the limitations inherent in the art of compounding such active components for therapeutic use in mammals as disclosed in this specification. Examples of suitable oral dosage forms in accord with this invention, for example, tablets, capsules, pills, powder packets, granules, wafers, cachets, teaspoonfuls, dropperfuls, ampules, vials, segregated multiples of any of the foregoing and other forms as herein described.

SPECIFIC EXAMPLES

In order that the present invention may be more fully understood, the following examples are given primarily by way of illustration. No specific details or enumerations contained therein should be construed as limitations on the present invention, except insofar as they appear in the appended claims. All parts and percentages are by weight unless otherwise specifically designated.

EXAMPLE 1

In this example, the test animal is a 296 kg. horse which is naturally infected with parasites. In the critical tests, efficacy evaluations are made to determine activity against naturally acquired infections of bots, ascarids, large and small strongyles and pinworms.

After weighing out the trichlorfon and levamisole hydrochloride for the desired dosage, 40 mg./kg. and 8 mg./kg. body weight, respectively, the materials are dissolved in combination in 250 ml. of deionized water. Gastric intubation is used to administer the solution, and the tube is rinsed with 250 ml. of deionized water to insure complete administration to the animal.

A complete collection is made of the feces excreted during a six-day interval between treatment and necropsy. At 24-hour intervals, feces are collected, weighed, crumpled, mixed and sampled by the removal of 500 g. for each 5,000 g. or fraction thereof. The sample is fixed by saturation with 10% formalin solution, and the remains are carefully picked through to count the large parasites (bots, ascarids, pinworms and large strongyles).

The animal is killed and necropsied after a six-day post-treatment interval, and a complete examination is made of the contents and linings of the gastrointestinal tract for the large parasites. In addition, a sampling procedure similar to that described for the feces is employed on the cecal, ventral colon, and dorsal colon contents to estimate the number of small parasites.

In this particular case, the combination is effective in the removal of 96% of the small strongyles. The combination is also effective in the removal of the most pathogenic large strongyle, *Strongylus vulgaris* and bots (*Gasterophilus spp.*). The results are summarized in Table I.

TABLE I

Critical Activity of Levamisole.HCl/Trichlorfon in Horses

| Percent Removal[a] | | | | |
|---|---|---|---|---|
| Large Strongyles | | Small Strongyles | Bots | |
| S.v. | S.e. | | G.i. | G.n. |
| 96 | 58 | 96 | 99 | 100 |
| 100 | 67 | 93 | 97 | 100 |
| 100 | 100 | 85 | 59 | — |

[a] S.v. = Strongylus vulgaris
S.e. = Strongylus edentatus
G.i. = Gasterophilus intestinalis
G.n. = Gasterophilus nasalis

EXAMPLE 2

In this example, 1-6-phenyl-2,3,5,6-tetrahydroimidazo-[2,1-b]thiazole hydrochloride is administered orally to a horse at a dose level of 8 mg./kg. body weight. The results, summarized in Table II, shows that 1-6-phenyl-2,3,5,6-tetrahydroimidazo[2,1-b]thiazole hydrochloride is not very effective for removal of small strongyles from horses.

TABLE II

Critical Activity of Levamisole Hydrochloride at 8 mg./kg. Against Strongyles in Horses

| Percent Removal[a] | | | | |
|---|---|---|---|---|
| Large Strongyles | | Small Strongyles | Bots | |
| S.v. | S.e. | | G.i. | G.n. |
| 100 | 47 | 24 | <1 | 0 |

EXAMPLE 3

In this example, 0,0-dimethyl (2,2,2-trichloro-1-hydroxyethyl)phosphonate was administered orally to four horses at a dosage level of 40 mg./kg. body weight. The results, summarized in Table III, show that 0,0-dimethyl (2,2,2-trichloro-1-hydroxyethyl)phosphonate at 40 mg./kg. body weight is not very effective for the removal of either large or small strongyles from horses.

TABLE III

Critical Activity of Trichlorfon at 40 mg./kg. Against Strongyles in Horses

| Percent Removal | | |
|---|---|---|
| Large Strongyles | | Small Strongyles |
| Strongylus vulgaris | Strongylus edentatus | |
| 10 | 5 | 30 |

I claim:

1. An anthelmintic composition for controlling strongyles in equine species comprising 0,0-dimethyl (2,2,2-trichloro-1-hydroxyethyl)phosphonate and 1-6-phenyl-2,3,5,6-tetrahydroimidazo[2,1-b]thiazole hydrochloride in an amount of from 4 grams to about 40 grams in a weight ratio of 5 parts by weight of 0,0-dimethyl (2,2,2-trichloro-1-hydroxyethyl)phosphonate to each part by weight of 1-6-phenyl-2,3,5,6-tetrahydroimidazo[2,1-b]-thiazole thiazole hydrochloride.

2. A method for controlling strongyles in equine species, which comprises administering orally or parenterally to said infested equine species an anti-strongyles effective amount of a composition of 5 parts by weight of 0,0-dimethyl (2,2,2-trichloro-1-hydroxyethyl)-phosphonate to each part by weight of 1-6-phenyl-2,3,5,6-tetrahydroimidazo[2,1-b]thiazole hydrochloride.

* * * * *